(12) United States Patent
Liotta et al.

(10) Patent No.: US 9,012,240 B2
(45) Date of Patent: Apr. 21, 2015

(54) HYDROGEL NANOPARTICLE BASED IMMUNOASSAY

(75) Inventors: Lance A. Liotta, Bethesda, MD (US); Alessandra Luchini, Fairfax, VA (US); Emanuel F. Petricoin, Gainesville, VA (US); Virginia Espina, Rockville, MD (US)

(73) Assignee: George Mason Research Foundation, Inc., Fairfax, VA (US)

( * ) Notice: Subject to any disclaimer, the term of this patent is extended or adjusted under 35 U.S.C. 154(b) by 158 days.

(21) Appl. No.: 13/061,507

(22) PCT Filed: Aug. 26, 2009

(86) PCT No.: PCT/US2009/055060
§ 371 (c)(1),
(2), (4) Date: Jun. 8, 2011

(87) PCT Pub. No.: WO2010/025190
PCT Pub. Date: Mar. 4, 2010

(65) Prior Publication Data
US 2011/0236999 A1    Sep. 29, 2011

Related U.S. Application Data

(60) Provisional application No. 61/091,935, filed on Aug. 26, 2008.

(51) Int. Cl.
*G01N 33/549* (2006.01)
*G01N 33/53* (2006.01)
*G01N 33/544* (2006.01)
*G01N 33/558* (2006.01)
*G01N 33/52* (2006.01)
*G01N 33/543* (2006.01)

(52) U.S. Cl.
CPC ........ *G01N 33/521* (2013.01); *G01N 33/54333* (2013.01); *G01N 33/54346* (2013.01)

(58) Field of Classification Search
CPC .......... G01N 33/558; G01N 33/54306; G01N 33/54346; B22F 1/0018; B82Y 30/00; B82Y 15/00; Y10S 435/97; A61K 49/0428
See application file for complete search history.

(56) References Cited

U.S. PATENT DOCUMENTS 7,425,302 B2 *  9/2008  Piasio et al. .................. 422/412

OTHER PUBLICATIONS

Luchini et al. Smart hydrogel particles: biomaker harvesting: one step affinity purification, size exclusion, and protection against degradation. Nano Letters 2008, vol. 8, No. 1, pp. 350-361.*
Nayak et al. Ligand-functionalized core/shell microgels with permselective shells. Angew. Chem. Int. Ed. 2004, vol. 43, pp. 6706-6709.*

* cited by examiner

*Primary Examiner* — Shafiqul Haq
(74) *Attorney, Agent, or Firm* — Michael L. Greenberg, Esq.; Greenberg & Lieberman, LLC

(57) ABSTRACT

An immunoassay device incorporating porous polymeric capture nanoparticles within either the sample collection vessel or pre-impregnated into a porous substratum within fluid flow path of the analytical device is presented. This incorporation of capture particles within the immunoassay device improves sensitivity while removing the requirement for preprocessing of samples prior to loading the immunoassay device. A preferred embodiment is coreshell bait containing capture nanoparticles which perform three functions in one step, in solution: a) molecular size sieving, b) target analyte sequestration and concentration, and c) protection from degradation. The polymeric matrix of the capture particles may be made of co-polymeric materials having a structural monomer and an affinity monomer, the affinity monomer having properties that attract the analyte to the capture particle. This device is useful for point of care diagnostic assays for biomedical applications and as field deployable assays for environmental, pathogen and chemical or biological threat identification.

1 Claim, 13 Drawing Sheets

A.

B.

A.

B.

C.

A.

B.

C.

HYDROGEL NANOPARTICLE BASED IMMUNOASSAY

REFERENCE TO RELATED APPLICATIONS

This application claims an invention that was disclosed in Provisional Application No. 61/091,935, filed Aug. 26, 2008, entitled "Hydrogel Nanoparticle based Immunoassay". Priority is hereby claimed. The benefit under 35 USC §119(e) of the United States provisional application is hereby claimed, and the aforementioned application is hereby incorporated herein by reference.

GOVERNMENT LICENSE RIGHTS

This invention was made with government support under DE-FC52-04NA25455, awarded by the Department of Energy. The government has certain rights in the invention.

FIELD OF THE INVENTION

This invention relates to the incorporation of hydrogel nanoparticles into a point of care immunoassay, such as a lateral flow immunoassay or immunochromatographic strip device, as part of the sample collection vessel or immobilized within the fluid flow zones. More particularly, the invention relates to a portable immunoassay device containing a population of harvesting hydrogel nanoparticles capable of molecular sieving, target analyte sequestration and concentration in addition to analyte protection from degradation.

BACKGROUND OF THE INVENTION

Lateral flow assays (LFA) have been used successfully as a diagnostic tool for more than 15-years. They provide point of care (POC) diagnosis without requiring expansive clinical laboratories and specifically trained technical staff. LFA devices are generally considered inexpensive to manufacture, have long shelf-lives and have minimal storage requirements. LFA diagnostic results are read either through visual inspection of the chromatographic strip or through the use of a spectrophotometer 'reader' instrument. Visual inspection of the assay results is typically limited to a yes/no or positive/negative result.

Both visual and reader measurements are considered qualitative or semi-quantitative and not sensitive enough to quantitatively assess low-abundance biomarker levels. Current LFA designs for POC use are also limited due to their inability to precondition complex biological fluids prior to immunoassay analysis. These limitations reduce LFAs sensitivity for low abundance analytes and biomarkers while, concurrently, minimizing their effectiveness as a POC diagnostic device for low abundance biomarkers, and other low molecular weight compounds.

A major challenge when using a POC immunoassay as a diagnostic device is the ability to process complex biological fluids without standard lab equipment. In many cases, a centrifuge may be required to pre-condition blood samples to provide a plasma sample or to remove cells from blood samples. Incorporation of coreshell hydrogel nanoparticles with molecular sieving and target analyte sequestration provides a unique solution to this limitation. Hydrogel nanoparticles designed with specific sieving and affinity characteristics act as a filter, concentrator, and protector of target analytes from degradation prior to analysis. These functions offer a novel solution to address major analytical challenges in biomarker discovery and diagnostic assays for low abundance analytes.

Another major challenge for LFA devices are their sensitivity for specific analytes of interest. The inability to precondition samples prior to analysis leads to poor sensitivity, high background interference and diluted samples. Incorporation of hydrogel nanoparticles into the device as a means of sample preconditioning significantly improves sensitivity by sequestering and concentrating only the targeted analyte prior to extraction from the particles into the immunoassay.

SUMMARY OF THE INVENTION

Lateral flow immunoassays in the prior art are typified by a sandwich type immunoassay in which one member of the antibody pair is labeled with a visual or signal-generating tag such as a gold colloid particle or a colored bead, while the other member of the antibody is bound to the solid phase. The analyte incubated with the labeled member of the antibody pair and the mixture is allowed to wick across the immobilized antibody member of the pair. If an analyte is present then a sandwich will form between the labeled antibody and the immobilized antibody thereby providing a detectable signal in the region of the immobilized antibody. The present invention provides a means to utilize porous hydrogel nanoparticles containing an analyte affinity bait as a means to preprocess and pre-concentrate and preserve the analyte of interest. The invention provides a means to improve the sensitivity of the immunoassay and protect the analyte from degradation in a point of care setting or outdoors. In one embodiment the analyte in the sample fluid (e.g. urine or blood) is introduced into a collection chamber which contains the nanoparticles in a dried form. The nanoparticles become dispersed in the sample and immediately sequester the target analyte. Sequestration efficiency greater than 99 percent has been achieved with a wide variety of analytes. The sequestered analyte is uniquely protected from degradation because it is immobilized to the affinity bait within the particle. In this manner the total content of analyte in a large sample volume can be concentrated into a small volume of particles. The volume concentration factor can be ten to 100-fold. Following exposure of the sample fluid containing the analyte to the nanoparticles, under the subject invention, the sample fluid containing the particles is allowed to passively wick into a permeable porous matrix such as nitrocellulose, cellulose acetate, porous glass, glass fibers, or paper. The pore size of the wicking material is chosen such that the particles do no migrate within the porous matrix. Following this step the particles are trapped at the entry point of the fluid to the porous matrix and the complete volume of the sample fluid will have wicked through the trapped nanoparticles. At this point the trapped analyte within the particles is completely harvested from the starting sample solution concentrated in a much smaller volume and is protected from degradation, because it is bound to the affinity bait. At this point the collected analyte, now stabilized in a small volume, can be stored or shipped.

At the time the user is ready to measure or analyze the trapped analyte existing within the nanoparticles, it is only necessary to introduce an elution buffer which detaches the bound analyte from within the nanoparticles and permits the elution and capillary wicking of the concentrated analyte into the analysis device. In one of the preferred embodiments the output eluate of the nanoparticles flows directly into the input of a standard sandwich immunoassay for full measurement. As shown in FIGS. 1-3, the lateral flow assay device is configured such that it can be in one of two states. In state one the sample fluid which had contained the analyte wicks away as waste and does participate in the downstream immunoassay. In state two an elution buffer is introduced and the fluid permeation path is altered so as to permit the eluate to enter a sandwich immunoassay. Such state change switches the fluid permeation path at the point of exit the analyte from the trapped nanoparticle. As shown in the figures, this can be accomplished by flexing two wicking matrix strips so that they come into contact and divert the flow into the immunoassay entry point where it encounters the labeled antibody. In a further embodiment the nanoparticles are pre loaded into the wicking matrix (instead of the particles being suspended in the starting sample solution) such that the sample fluid containing the analyte is passively or actively filtered through the nanoparticles to accomplish the nanoparticle sequestration of the analyte.

The capture particles in this invention are hydrogel nanoparticles comprising: a) a molecular sieve portion; and b) an analyte binding portion; wherein the molecular sieve portion, analyte binding portion or both further comprise a crosslinked region having modified porosity. The nanoparticles are used to harvest, concentrate, and protect target analytes from degradation.

In one embodiment, the current invention describes the incorporation of hydrogel nanoparticles into either the fluid collection vessel or the porous substratum as part of a microfluidic immunoassay device. The hydrogel nanoparticles function as a means to sequester, concentrate and protect protein, peptide, or nucleic acid based biomarkers or other low molecular weight analytes from degradation.

In another embodiment the current invention describes a method of which hydrogel nanoparticles can be immobilized within the fluid zones of the immunoassay device. The hydrogel nanoparticles may be impregnated within a porous matrix chamber for sample deposition. Sample fluids (can be biological or non-biological) pass through the hydrogel nanoparticle chamber allowing for the sequestration of desired analytes within the nanoparticles and the wicking away of unwanted sample fluids.

In another embodiment the current invention describes the method of which hydrogel particles can be contained within a sample collection device. Hydrogel nanoparticles located in a sample collection device allows for the molecular size sieving, affinity analyte sequestration, concentration and protection from degradation. The remaining sample fluid is wicked away from the collection device and an extraction buffer is used to transport the desire analytes through an immunoassay device.

Another embodiment describes a lateral flow immunoassay containing a population of harvesting nanoparticles containing multiple subpopulation specific for individual classes of low molecular weight molecules present in whole blood and other body fluids such as urine cerebro-spinal fluid, sweat, saliva, nipple aspirates, breath condensate, bronchoalveolar lavage fluid and amniotic fluid, as well as non-biological fluids such as environmental water samples. A device containing multiple subpopulations may provide a means to simultaneously quantify multiple analytes in a single device configuration.

The black boxes represent striped boxes represent light blots on the graphic.

DETAILED DESCRIPTION OF THE PREFERRED EMBODIMENT(S) INVENTION

Figure 1:
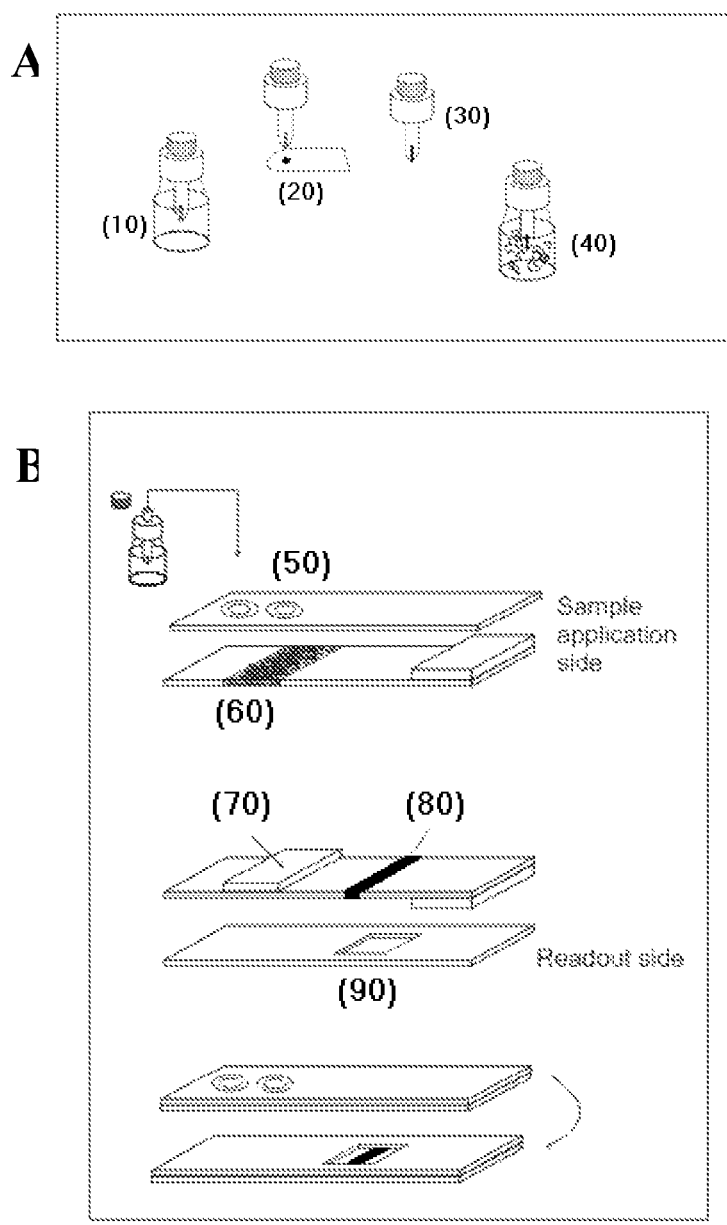
FIG. 1a shows a method of sample collection using a collection device (10) that pretreats the sample fluid prior to applying in to the lateral flow immunoassay device. A blood sample is taken from a finger (20), and known quantity of blood fills the capillary slot the sample collection device (30). The sample is then dispersed in a buffer (40), where it becomes pretreated for the LFA.
FIG. 1b shows a design of lateral flow immunoassay device with nanoparticles impregnated into substratum. On the sample application side, there are two compartments (50); one to add the pretreated sample and one to add the eluate. There is also a portion of the strip that is impregnated with nanoparticles (60). On the readout side, there is a portion of the strip that contains antibodies and gold particles (70). There is also a portion that contains another set of antibodies that create a sandwich assay (80). Over this second group of antibodies is a readout window (90).

As shown in FIG. 1a, a uniform volume of sample can be collected by a capillary slot on the end of a wand that is an integral part of a dropper vial containing a sample diluent. This is a means to collect a sample from a finger stick of blood in the field and to perform a reproducible volume dilution. The dilution vial can contain the nanoparticles of the invention in suspension. The sample in the dropper vial is introduced into the device such that a funnel shaped orifice receives the sample containing the nanoparticles in solution and the nanoparticles containing the analyte are filtered out at the wicking entry point.

Once the method shown in FIG. 1a is complete, the pretreated sample undergoes a two-step method of analysis within a lateral flow immunoassay device, as shown in FIG. 1b. The immunoassay device comprises: a) a sample application side, and b) a readout side that are sandwiched together. The sample application side is a strip that contains two separate slots at one end through which the pretreated sample and elution buffer are added, and an absorbent pad at the opposite end of the strip. In between the two ends, beneath one of the slots, there is a section of the strip which is impregnated with capture particles. The readout side of the device comprises a) a region under the capture particles containing antibodies and gold particles that are attracted to one epitope of the target analyte, b) a region of antibodies that are attracted to a different epitope of the target analyte than the first region of antibodies, c) a readout window around the second region of antibodies, and d) an absorbent pad. In the first step of the method illustrated in FIG. 1b, a pretreated sample is added to the first slot. The sample moves down the length of the strip, passing through the region of capture particles. The capture particles harvest the target analyte from the sample, and the rest of the sample is wicked away to the absorbent pad at the end. Once the first step is complete, an elution buffer is added to the second slot directly over the region of capture particles that now contain the target analyte. The analytes are eluted from the capture particles, and travel to the region containing the first set of antibodies and gold particles. The antibodies attach to the target analytes, and the sample moves down the strip to the second region of antibodies. The target analytes attach to the second region of antibodies, becoming sandwiched between the two sets of antibodies. When this occurs, a color change is observed in the readout window of the device. The rest of the sample continues down the length of the strip to the absorbent pad at the end.

Figure 2:
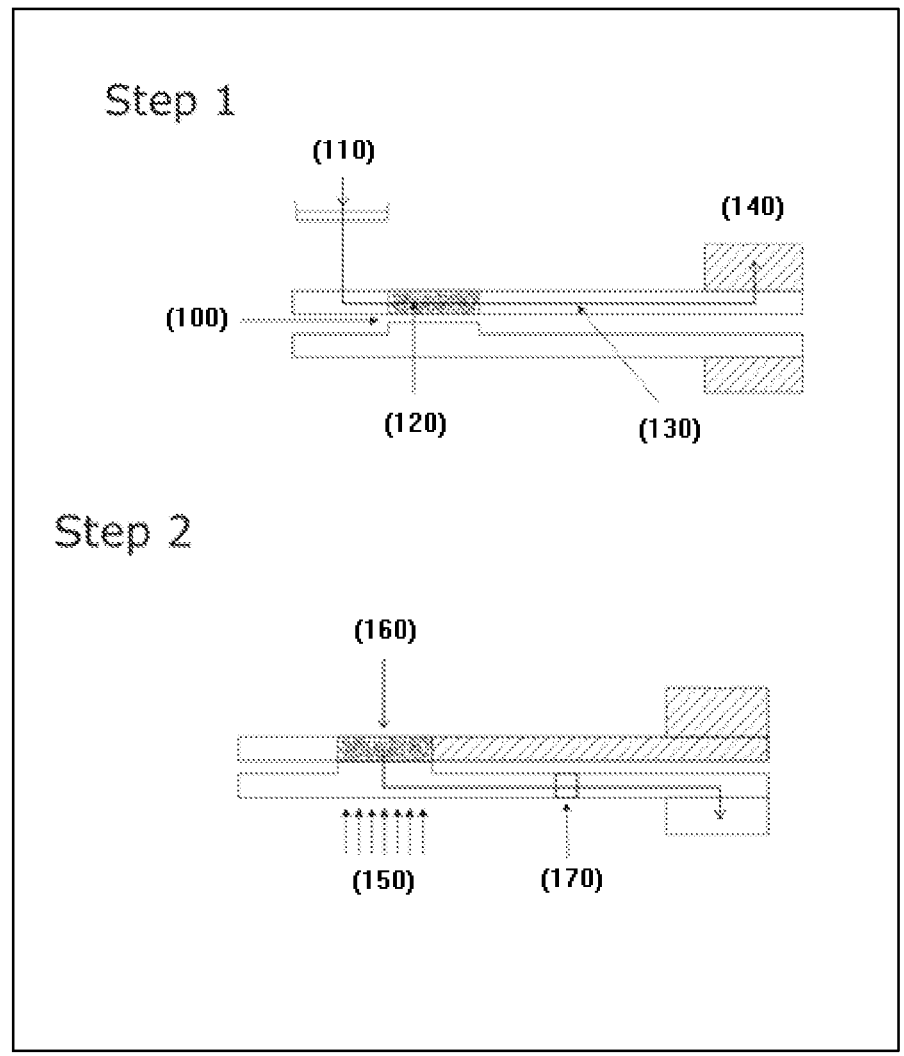
FIG. 2 shows a design of lateral flow immunoassay device with nanoparticles impregnated into substratum, where the sample application portion of the LFA is separate from the readout portion until the target analytes are eluted from the immobile hydrogel nanoparticles (100). The sample is added to the test strip (110), and then travels through a portion of nanoparticles that are impregnated on the strip (120). The fluid buffer and sample flow down the strip (130) until the fluid is absorbed at the end (140). The second step requires contact to be made between the nanoparticles and the first set of antibodies (150). After contact is made, the particles are eluted (160) and the target analytes travel down the strip to the read out line (170).

In another embodiment of the invention, the sample application and readout sides of the device are initially separated by an air gap, as shown in FIG. 2. In this embodiment, the region of capture particles comes in contact with the first region of antibodies during elution by pushing the two regions together, turning a knob, pulling out a separation tab, swelling of the sample application layer of the device, or by some other means of bringing the two regions into contact.

Figure 3:
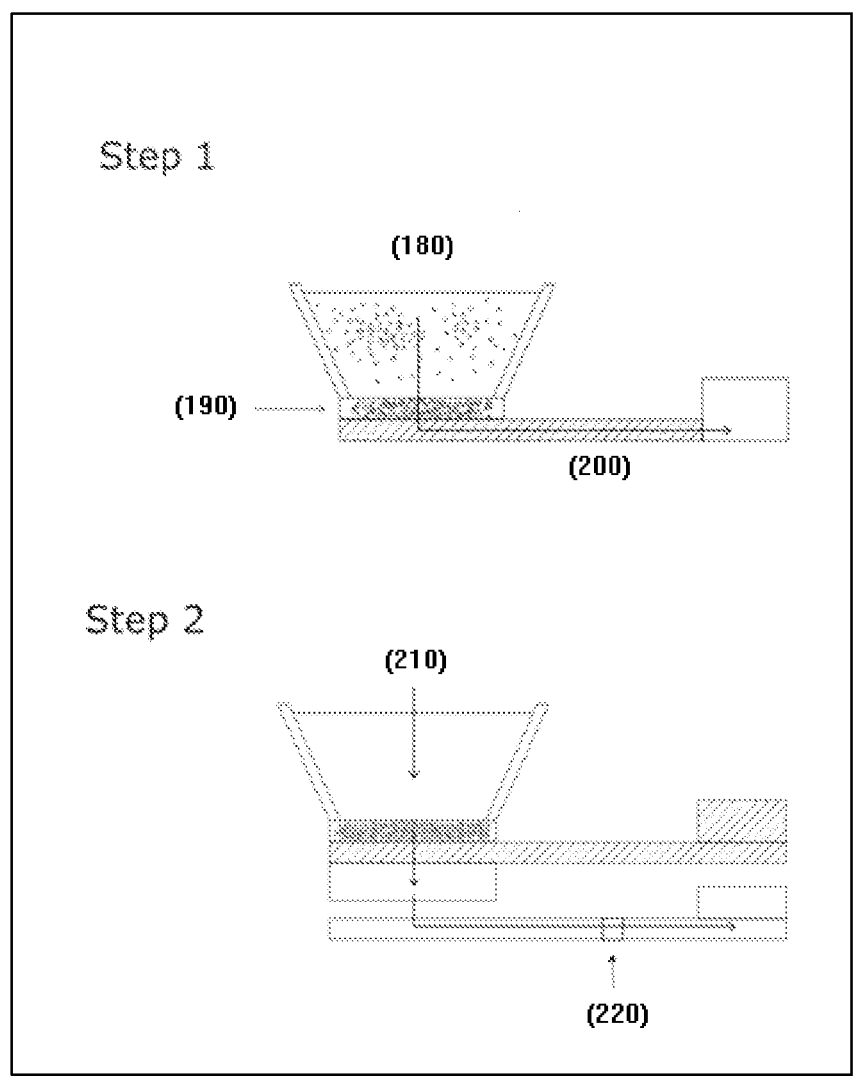
FIG. 3 shows a design of lateral flow immunoassay device with a loose mesh portion (190) to capture hydrogel nanoparticles that are mixed in with an initial sample instead of being impregnated into the LFA test strip. In step 1 of the diagram, the sample is introduced to the strip through a container adjacent to the mesh (180), and the buffer is wicked away down the length of the strip (200). In step 2 of the diagram, eluate is added above the nanoparticles (210), and the target analytes travel down the strip to the readout window (220).

In another embodiment of the invention, the capture particles are added directly to the sample rather than being impregnated in the lateral flow device, as shown in FIG. 3. Once the capture particles have harvested the target analyte, the first step of the lateral flow immunoassay occurs when the sample is then applied to a sample site on the device, with a loose mesh section that traps the capture particles while the rest of the sample is wicked away to the absorbent pad on the end. The second step involves the addition of an extraction buffer to the loose mesh which extracts the target analytes from the capture particles, allowing the analytes to travel through the sandwich assay contained in the readout side of the device, as shown in FIG. 3.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

EXAMPLE 1

1. The foremost problem in biomarker measurement is the extremely low abundance (concentration) of candidate markers in blood, which exist below the detection limits of mass spectrometry and conventional immunoassays. Such a low abundance would be expected for early stage disease since the diseased tissue constitutes a small proportion of the patient's tissue volume. Early-stage disease detection generally provides better overall patient outcomes.
2. The second major problem for biomarker discovery and measurement is the overwhelming abundance of resident proteins such as albumin and immunoglobulins, accounting for 90% of circulating plasma proteins, which confound and mask the isolation of rare biomarkers [6]. In fact, the vast majority of low abundance biomarkers are non-covalently and endogenously associated with carrier proteins, such as albumin, which exist in a billion fold excess compared to the rare biomarker [7].
3. A third serious challenge for biomarker measurement is the propensity for the low abundance biomarkers to be rapidly degraded by endogenous and exogenous proteinases immediately after the blood sample is drawn from the patient. Degradation of candidate biomarkers occurs also during transportation and storage of blood, generating significant false positive and false negative results [8].

The field of nanotechnology offers fresh approaches to address these three fundamental physiologic barriers to biomarker discovery. Recently, we have engineered smart hydrogel coreshell nanoparticles that overcome these three barriers and will do so in one step, in solution [9]. A hydrogel particle is a cross linked particle of sub-micrometer size composed of hydrophilic polymers capable of swelling and contracting as a result of the application of an environmental trigger, e.g., temperature, pH, ionic strength or electric field [10-14].

Hydrogel particles have extensive applications in biomedicine and biotechnology [15-18] because of their high biocompatibility and unique physiochemical properties.

The nanoparticles simultaneously conduct molecular sieve chromatography and affinity chromatography in one step in solution [9]. The molecules captured and bound within the affinity matrix of the particles are protected from degradation by exogenous or endogenous proteases. Despite the promise of this feasibility study [9], it remained to be proven whether such hydrogel particle technology could be shown to be applicable to a clinically relevant, highly labile, and very low abundance biomarker. To address this challenge we created a new class of core-shell particles and tailored the core bait to specifically capture a model biomarker Platelet Derived Growth Factor (PDGF). In order to study the applicability of hydrogel particles to a real world problem, PDGF was chosen as a highly challenging model for cancer related biomarker analysis because it is present in blood in extremely low concentration (3 ng/mL), with a short half life (2 minutes) [1,2]. The PDGFs are a family of peptide growth factors that signal through cell surface tyrosine kinase receptors and stimulate various cellular functions including growth, proliferation, and differentiation. Four different polypeptide chains (PDGF-A, -B, -C, and -D) encoded by different genes (chromosomes 4, 7, 11, 22) have been described [19, 20]. PDGF plays a role in angiogenesis and the level of tumor interstitial pressure during tumor progression [21-23]. Several new therapeutic agents designed to target PDGF and its receptor are presently in use in the oncology clinic [24-28]. Despite this known theranostic value, PDGF cannot be measured routinely and accurately in the clinic because of the extreme low abundance and high instability of this low molecular weight growth factor. Beyond PDGF, the sequestration and protection from degradation for a series of additional very low abundance and very labile chemokines such as CCL28, CCL24, and CXCL12 were verified. These chemokines have a concentration in serum of 44 pg/mL [29], 103 pg/mL [30], and 1.5 ng/mL [31], respectively. The half life of chemokines in blood is very short, less than ten minutes [32]. Chemokines are small cytokines that direct migration of leukocytes, activate inflammatory responses and participate in tumor growth. Chemokines modulate tumor behavior by three important mechanisms: regulation of tumor-associated angiogenesis, activation of a host tumor-specific immunological response, and direct stimulation of tumor cell proliferation in an autocrine fashion. All of these mechanisms are promising drug targets [33].

The incorporation of a bait molecule in the porous latex if hydrogel particles drives the uptake of molecules in solution, shifts the equilibrium towards association with the particles, and assures that captured molecules are preserved from degradation. The bait can be introduced via copolymerization of a monomer carrying the chemical moiety or via loading the chemical moiety with covalent bonding to an already formed hydrogel particle.

A menu of bait chemistries has been created to selectively bind and concentrate a diverse range of biomarkers, such as a) proteins and peptides, b) metabolites, c) lipids and fatty acids, d) nucleic acids, and e) post translationally modified peptides (e.g. glycosylated and phosphorylated). Bait chemistries include charge-based bait (acrylic acid, allylamine co-monomer), triazine loaded dye (cibacron blue), beta-cyclodextrin, boronic acid.

Acrylic acid is deprotonated at pH values greater than 3.5 and therefore carries a negative charge that targets positively charged polypeptides and proteins. Allylamine (pK=9.69 [34]) acts as a bait for polypeptides and proteins that have net negative charge. The affinity of polypeptides to charged particles has been proven to be higher than the affinity of polypeptide for carrier proteins and depends on the value of the isoelectric point of proteins and the dissociation constant of particles [9]. Harvesting and concentration properties of charged particles 141 depend on the pH and ionic strength of the solution.

An alternative bait strategy is to load NIPAm based particles with triazine derived textile dyes (Cibacron blue F3G-A, Procion red H8BN) [35]. Dyes have been used in affinity chromatography for their low cost and highly specific molecular recognition [36]. We have successfully synthesized Cibacron Blue dye loaded hydrogel particles and demonstrated their efficacy for uptake small proteins and hormones from urine [37].

Additionally, cyclodextrins were coupled to hydrogel particles. Cyclodextrins are cyclic glucose oligosaccharides that have lipophilic inner cavities and hydrophilic outer surfaces that are capable of interacting with hydrophobic guest molecules to form noncovalent complexes, and have been extensively used as vector for drug delivery [38]. Cyclodextrin have been shown to bind cholesterol [39], steroids [40], DOPA [41]. Hydrogen bonds, Van der Waals interaction, electrostatic interactions are thought to be the forces that attract and stabilize guest molecules that have suitable size and preferably hydrophobic character [42].

Furthermore, we designed particles that contain boronic acid groups, which are known to form complexes with diol groups of target biomolecules. Boronate ion has been used for affinity chromatography applications involving the selective isolation of nucleotides, RNA, glycated proteins and glycoenzymes [43-48].

In a core-shell architecture, the bait containing region is covered by a porous shell. Core-shell hydrogel particles are of special utility because the properties of the core and shell can be tailored separately to suit a particular application. In many core-shell particle systems used for drug delivery, the core is designed to have the properties required for its intended application [12, 49-51]. The shell is then separately added to surround and shield the core. The thickness of the shell can be modified to alter permeability or porosity.

Figure 4:
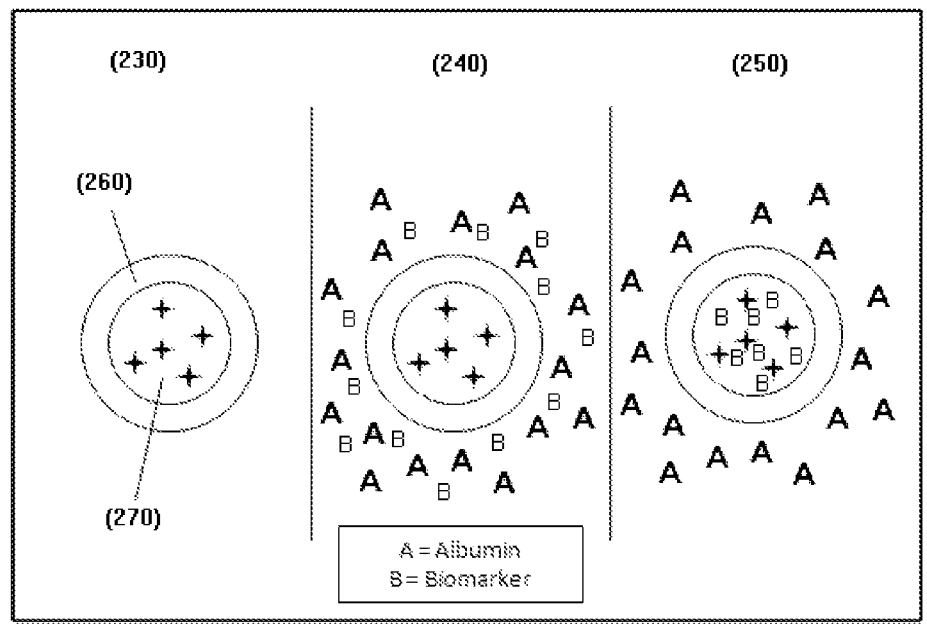
FIG. 4 shows a schematic illustration of core shell particle (230). The nanoparticle consists of a NIPAm-AAc core (270) that functions as a bait. After adding particles to the protein solution (240), biomarkers are attracted and entrapped in this bait (250). A NIPAm shell (260) increases the sieving properties of nanoparticles.

In the present study, we synthesized a core-shell particle in which a N-isopropylacrylamide (NIPAm)-acrylic acid (AAc) core contains a charge based bait to perform affinity binding to proteins in solutions, and a NIPAm shell surrounds the core and acts as a sieve to exclude solution phase proteins too large to penetrate the porosity of the shell (FIG. 4). NIPAm based particles exclude larger molecules with a sharp molecular size cut off due to their porous structure. The degree of porosity can be tuned by changing the percentage of cross-linker N,N' methylenebisacrylamide (BIS) with respect to the monomer. At the same time, particles can imbibe large amounts of water which provide favorable conditions for polypeptides and other small molecules to penetrate the polymer matrix, and also allow concentration of rare protein biomarkers [14].

We used three independent experimental systems to test whether the new particles could accomplish the following a) Rapidly harvest all of the solution phase PDGF and chemokine molecules within a complex mixture of high abundance proteins including whole serum, b) Release the captured PDGF and chemokine into a small volume that was a fraction of the starting volume, while completely excluding high abundance proteins such as albumin. This concentration step has the potential to magnify the detectable level of the marker in a small volume that is required for input into a measurement system such as an immunoassay platform or mass spectrometry, and c) Protect the captured PDGF and chemokine from degradation by exogenous degradative enzymes introduced at high concentration. The three independent experimental approaches employed for the present study were 1) A clinical grade ELISA immunoassay, 2) Gel Electrophoresis of the starting solution, the supernatant and the particle contents followed by immunoblotting, and 3) Mass Spectrometry analysis of the starting solution compared to the particle capture eluate.

The purpose of this study was to explore the capacity of the core-shell particles to concentrate and preserve biomarkers as theoretically envisioned.

Results

Particle Synthesis and Characterization

Figure 5:
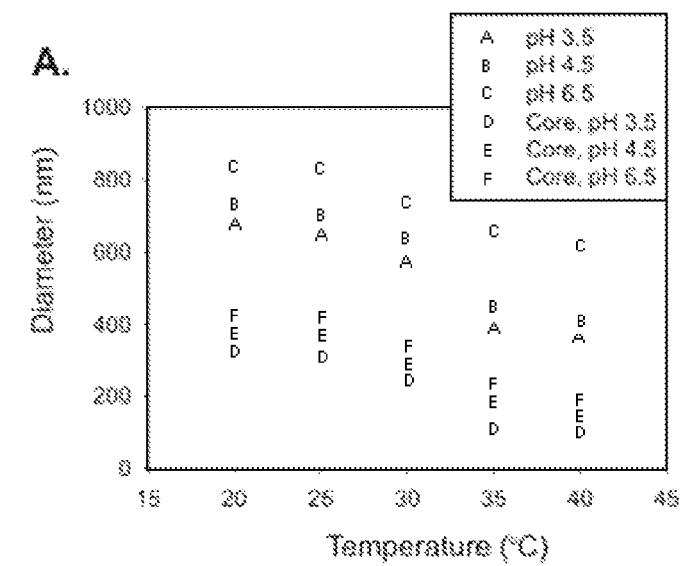
FIG. 5 shows light scattering and atomic force microscopy characterization of nanoparticles. (A) At room temperature, core is approximately 360 nm in size whereas adding core-shell particles have a diameter of 700 nm at pH 4.5. Core and core shell particles follow a typical temperature dependent behavior. (B) Particle suspension in MilliQ water (pH 5.5, 1 μg/mL) was deposited on freshly cleaved mica under humid atmosphere at room temperature for 15 minutes and dried under nitrogen. Atomic force microscopy (AFM) image of nanoparticles was acquired. Particles have a diameter of approximately 800 nm and exhibit a homogeneous size distribution. The scale bar for particle height shows a maximum height of 168 nm. The AFM picture was acquired under dry status therefore the particles are distorted (flattened) from their spherical shape due to drying on the mica surface.
Figure 5:
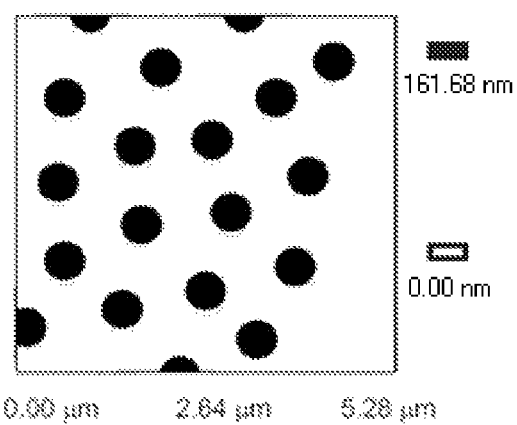

For the particle architecture used in the present study, a NIPAm shell surrounds a NIPAm/AAc core, containing affinity bait moieties. The sieving capability of the NIPAm shell shields the core and its affinity bait groups from larger molecules that may be present and could compete with the intended low-abundance, low molecular weight molecular targets for binding to the affinity bait in the core. Light scattering characterization was conducted on the particles during synthesis and at the end of the process in order to compare the sizes of the core and the core-shell particles. The core diameter at 25° C. and pH 4.5 is 364.7+/−4.3 nm whereas the diameter of the core-shell particles at the same conditions is 699.4+/−6.2 nm (FIG. 5A). This suggests that the thickness of the shell is about 170 nm Following the characteristic behavior of AAc containing hydrogels, both the core and the core-shell particle size decreased with increasing temperature and decreasing pH (FIG. 5A). Particles were further characterized by means of atomic force microscopy (AFM). AFM particle images (FIG. 5B) confirm size homogeneity, and AFM particle diameter readings were consistent with those measured with light scattering. Particle concentration, as obtained by weighing the lyophilized particles, was 10 mg/mL, and the number of particles per milliliter was 230 million.

Molecular Sieving and Concentration of PDGF by Core-shell Particles

Figure 6:
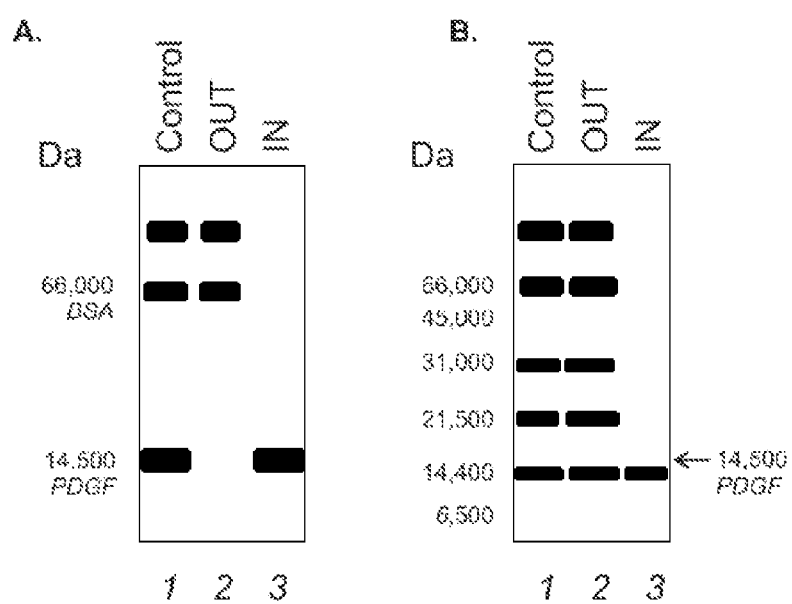
FIG. 6 shows SDS-PAGE Analysis of PDGF incubated particles. (A) Lane 1) Starting solution containing BSA and PDGF (Control), 2) Supernatant (OUT); 3) Particle content (IN). Particles remove PDGF from carrier albumin with a total exclusion of albumin itself. (B) Lane 1) Starting solution containing PDGF, BSA, aprotinin (MW 6,500 Da), lysozyme (MW 14,400 673 Da), trypsin inhibitor (MW 21,500 Da), carbonic anhydrase (MW 31,000 Da), and ovalbumin (MW 45,000 675 Da) (Control), 2) Supernatant (OUT); 3) Particle content (IN). Particles harvest PDGF together with low molecular weight proteins and exclude proteins above ca 20,000 Da.

Human platelet derived growth factor (PDGF, MW 14,500 Da) was spiked in a solution containing bovine serum albumin (BSA, MW 66,000 Da) as carrier protein associated with the PDGF. Core-shell hydrogel nanoparticles added to the PDGF-BSA solution acted as a molecular sieve as evidenced by no detectable association of BSA with the particles, and the particles completely sequestered all the solution phase PDGF while completely excluding the BSA (FIG. 6A). This suggests that PDGF affinity for the bait was higher than that for carrier BSA. In order to further assess the molecular sieving properties of core-shell particles, a solution containing: PDGF, BSA, aprotinin (MW 6,500 Da), lysozyme (MW 14,400 Da), trypsin inhibitor (MW 218 21,500 Da), carbonic anhydrase (MW 31,000 Da), and ovalbumin (MW 45,000 Da), was used. The uptake of proteins by the particles was evaluated by SDS PAGE. Core-shell particles efficaciously captured and concentrated low molecular weight proteins with a weight less than 21,500 Da whereas proteins with high molecular weight remained excluded from the particles (FIG. 6B).

Concentration of PDGF in Solution by Core-shell Hydrogel Nanoparticles

We examined the nanoparticles ability to concentrate a dilute PDGF sample, at a concentration below the detection threshold of the ELISA, to determine if the concentration of PDGF could be increased by particle sequestration, rendering the PDGF measurable by the ELISA.

Figure 7:
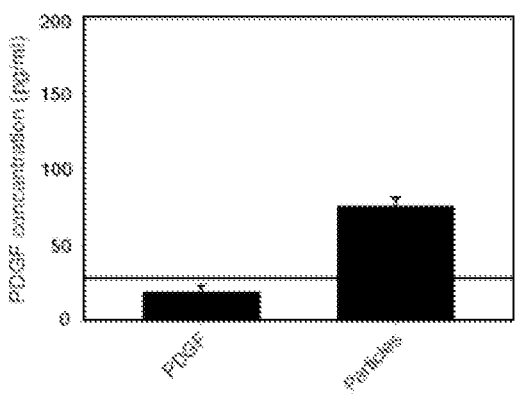
FIG. 7 shows core shell particles raise the concentration of undetectable PDGF into the detection range of ELISA assay. (A) ELISA readings of the starting solution of PDGF in Calibrator diluent RD6-3 (R&D Systems, animal serum with preservatives) at a concentration of 18.92+/−4.313 pg/mL and PDGF eluted from core-shell particles (85.27+/−2.24 pg/mL). (B) PDGF concentration in the core-shell particle eluate plotted against the quantity of particles utilized for the incubation, duplicate experiments. (C) ELISA standard 684 curve of PDGF concentration versus absorbance. The standard curve was generated with two repeats for each PDGF calibrator concentration.
Figure 7:
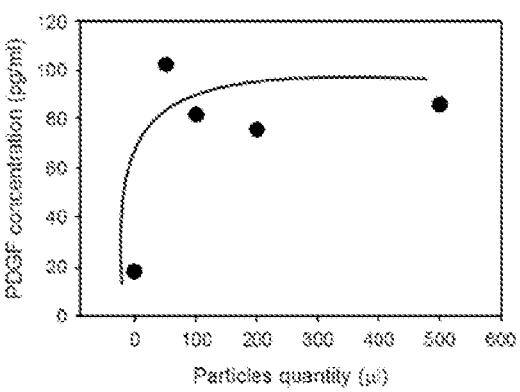
Figure 7:
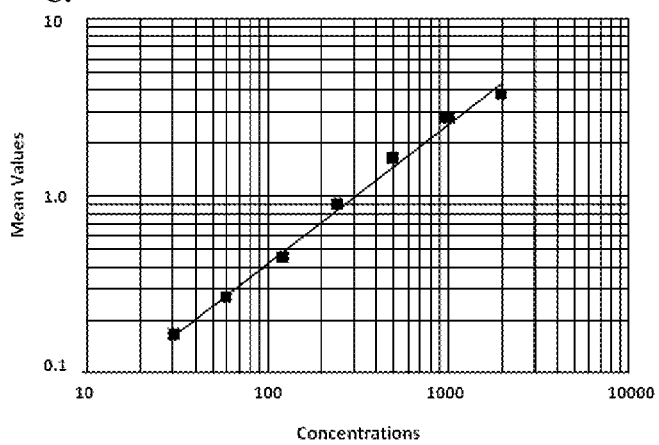
Figure 8:
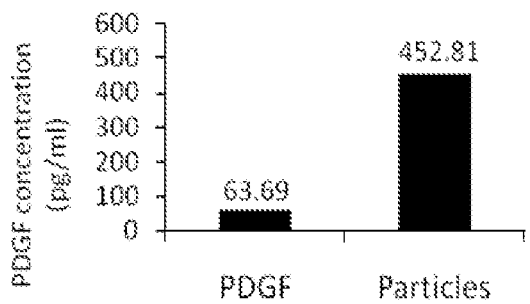
FIG. 8 shows core shell particles increase the concentration of extremely dilute PDGF approximately 10-folds (1000 percent) as measured by ELISA assay. (A) ELISA readings of the starting solution of PDGF in Calibrator diluent RD6-3 (R&D Systems, animal serum with preservatives) at a concentration of 63.69+/−1.448 pg/mL and PDGF eluted from core-shell particles (491.14+/−4.818 pg/mL). (B) PDGF concentration in core-shell particle eluate plotted against the quantity of particles utilized for the incubation, duplicate experiments. 694 (C) ELISA standard curve of PDGF concentration versus absorbance. The standard curve was generated with two repeats for each PDGF calibrator concentration.
Figure 8:
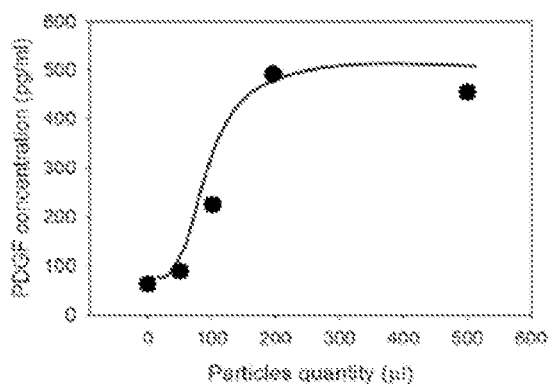
Figure 8:
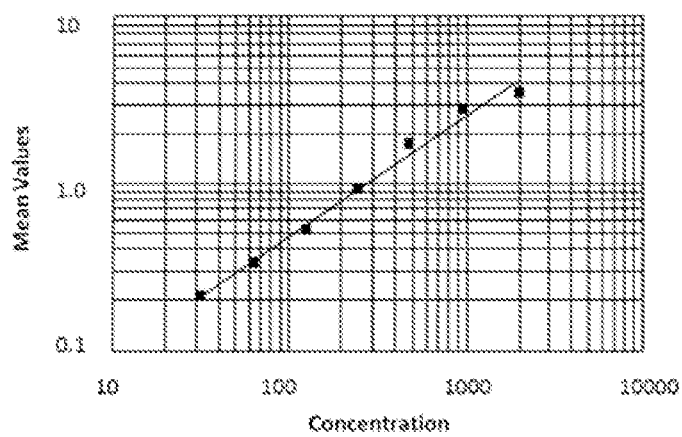

As shown in FIG. 6A, previously undetectable level of PDGF was recovered from the particles and successfully quantified by ELISA at concentrations ranging from 75 to 102 pg/mL. The value of PDGF concentration in the starting solution (18.92+/−4.313 pg/mL) reported in FIG. 7A was below the linear range of the ELISA immunoassay (minimum detectable PDGF dose=30 pg/mL) and was estimated by using the optical density and extrapolated from the 232 standard curve. Per manufacturer's instructions, the minimum detectable dose was determined by adding two standard deviations to the mean optical density value of twenty zero standard replicates and calculating the corresponding concentration. Therefore, core-shell particles, incubated with a PDGF solution at a concentration undetectable by ELISA, harvested and concentrated PDGF to a level higher than the detection limit of the assay. Saturation was reached with the minimum amount of particles when the PDGF solution was very dilute, as expected (FIG. 7B). A standard curve for PDGF ELISA assay was generated (FIG. 7C) in order to assess the quality of the procedure. A similar experiment was performed with a more concentrated PDGF solution. The concentration of PDGF in the starting solution was 63.69 (+/−1.448) pg/mL whereas the concentration of PDGF recovered from particles was 452.81 (+/−4.818) pg/mL yielding a concentration factor of about 700% (FIG. 8A). A PDGF solution was incubated with different volumes of particles and demonstrated that saturation was reached when the volume of particles was 200 μl (46 million particles, 1:5 v/v particles: PDGF solution ratio, FIG. 8B). The standard curve for PDGF ELISA assay was repeated (FIG. 8C).

Figure 9:
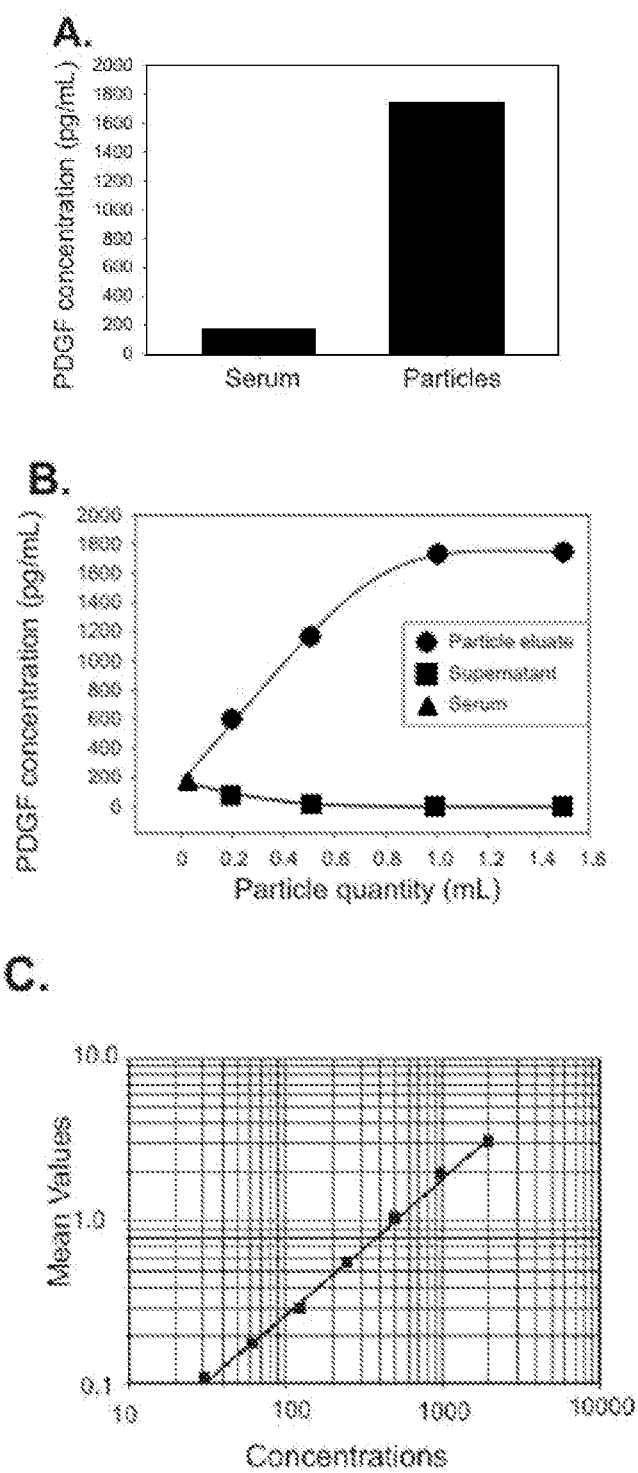
FIG. 9 shows core shell particles increase the concentration of native PDGF in serum as measured by ELISA assay. (A) ELISA readings of the starting serum solution in Calibrator diluent RD6-3 (R&D Systems, animal serum with preservatives) at a concentration of 170.91+/−4.66 pg/mL and PDGF eluted from core-shell particles (1743.43+/−11.06 pg/mL). (B) PDGF concentration in core-shell particle eluate plotted against the quantity of particles utilized for the incubation, duplicate experiments. (C) ELISA standard curve of PDGF concentration versus absorbance. The standard curve was generated with two repeats for each PDGF calibrator concentration.

A further experiment was performed in order to test the ability of core shell particles to sequester, concentrate and preserve native PDGF from human serum. We examined the effect of excess interfering proteins on the amount of particles necessary to reach saturation and complete depletion of native PDGF from serum. Serum was diluted 1:10 in Tris HCl 50 mM pH 7 and incubated with increasing quantities of particles (200, 500, 1000, and 1500 μL). The value of PDGF in the starting serum solution was read as 170.92+/−4.66 pg/mL whereas the concentration of PDGF recovered from particles was 1743.43+/−11.06 pg/mL yielding a concentration factor of about 10-fold (1000 percent) (FIG. 9A). Saturation was reached at a value of 1000 μL (230 million particles, 1:1 v/v particles:serum solution, FIG. 9B). Given the fact that the starting concentration of PDGF in serum is higher than the concentration of PDGF in the solution of FIG. 8, we can conclude that the presence of serum, with its enormous protein content in the starting sample, requires less than double amount of particles to deplete the sample, thus confirming the extremely high binding capacity of particles, even in the presence of abundant serum proteins. The standard curve for the PDGF ELISA assay used in these studies is shown (FIG. 9C).

Concentration of Chemokines in Solution by Core-shell Particles

Figure 10:
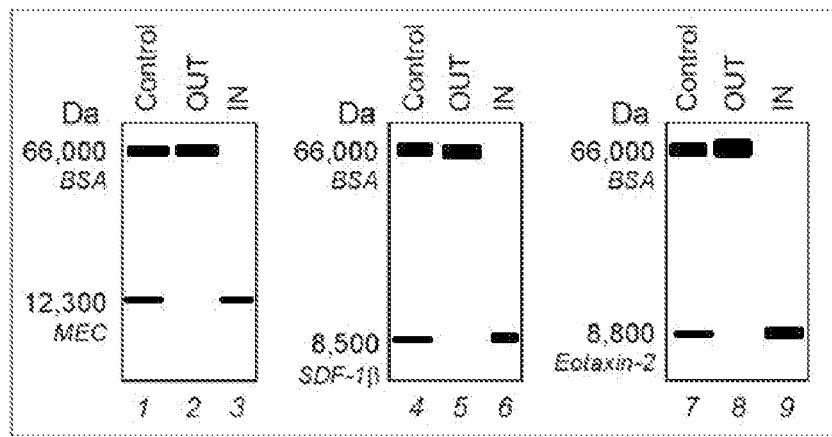
FIG. 10 shows SDS PAGE analysis showing chemokines uptake by particles. Core-shell particles were incubated with the following chemokines, mucosae-associated epithelial chemokine (MEC/CCL28), stromal cell-derived factor-1 beta, (SDF-1β/CXCL12b), and eotaxin-2 (CCL24), in presence of bovine serum albumin (BSA). Solutions of the chemokines and BSA are shown in lanes 1, 4, and 7. After incubation with the particles, no chemokine was left in the supernatant (S, lane 2, 5, and 8) and all the chemokine was captured by particles (P, lanes 3, 6, and 9). BSA was totally excluded by particles.

In FIG. 10 SDS PAGE analysis is shown on core shell acrylic acid functionalized particles incubated with other relevant models for serological biomarker, namely mucosae-associated epithelial chemokine (MEC/CCL28, 12,300 Da), stromal cell-derived factor-1 beta, (SDF-1β/CXCL12b, 8,500 Da), and eotaxin-2 (CCL24, 8,800 Da) mixed with BSA. Chemokines were totally removed from solution, captured and concentrated by particles, whereas BSA was completely excluded.

Protection from Enzymatic Degradation of PDGF by Core-shell Particles

Figure 11:
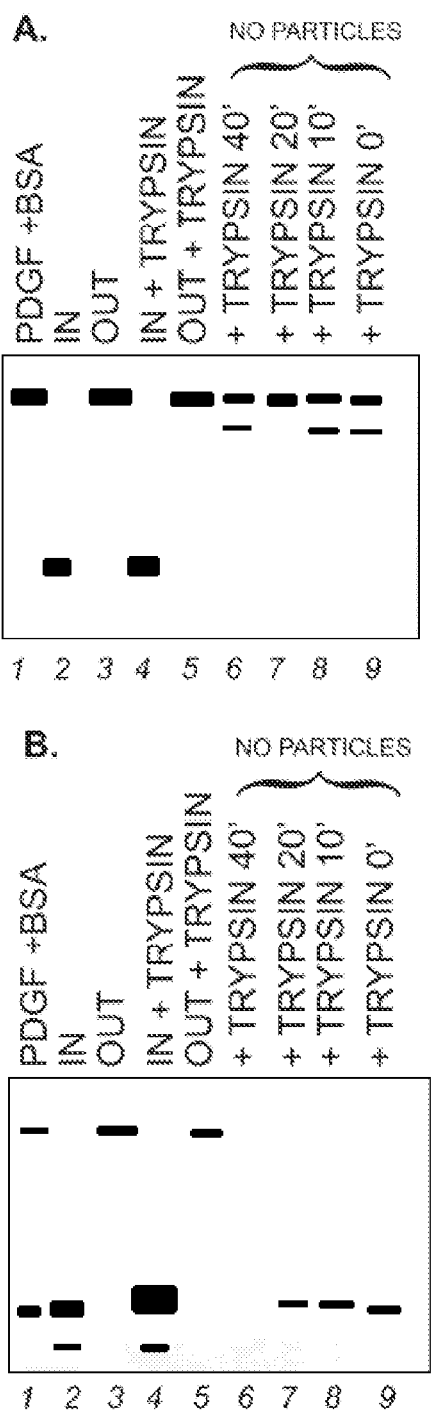
FIG. 11 shows immunoblot analysis showing that core-shell particles protect captured PDGF from tryptic degradation. (A) Sypro ruby total protein staining and (B) Immunoblot analysis with anti-PDGF antibody of the same PVDF membrane are presented. Lane 1) control PDGF+BSA solution; 2) content of particles incubated with PDGF+BSA (IN); 3) supernatant of particles incubated with PDGF+BSA (OUT); 4) content of particles incubated with BSA+PDGF+trypsin (IN+TRYPSIN); 5) supernatant of particles incubated with BSA+PDGF+trypsin (OUT+TRYPSIN); 6) BSA+PDGF+trypsin without particles incubated for 40 minutes (+TRYPSIN 40'); 7)) BSA+PDGF+trypsin without particles incubated for 20 minutes (+TRYPSIN 20'); 8)) BSA+PDGF+trypsin without particles incubated for 10 minutes (+TRYPSIN 10'); 9)) BSA+PDGF+trypsin without particles incubated for 0 727 minutes (+TRYPSIN 0').

Degradation of biomarkers by endogenous and exogenous proteases is a major source of biomarker performance bias, and hinders the discovery and measurement of candidate biomarkers. Immunoblot analysis was used to evaluate the particles ability to protect PDGF from enzymatic degradation. Trypsin action on PDGF in the absence of particles was evident after 10 minutes and almost complete after one hour, as indicated by nearly undetectable PDGF bands at 14,000-17,000 Da (FIG. 11A and FIG. 11B Lanes 6-8). In marked contrast, PDGF incubated with trypsin and core-shell particles generated a single species band that was not diminished in staining intensity and was not fragmented, suggesting that particles successfully preserved PDGF from proteolysis (FIG. 11A and FIG. 11B Lane 4). The PDGF band for the particles loaded with PDGF without trypsin (FIG. 11A and FIG. 11B Lane 2) was identical to that for the particles loaded with PDGF and trypsin (FIG. 11A and FIG. 11B Lane 4) further suggesting that no PDGF protein was lost because of enzymatic degradation.

Protection from Enzymatic Degradation of Chemokines by Core-shell Particles

Figure 12:
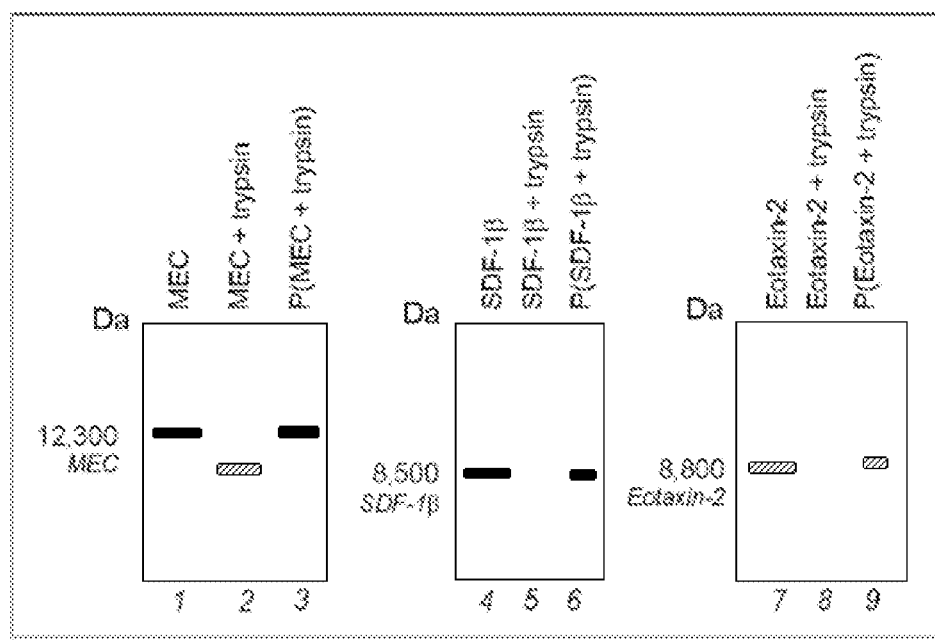
FIG. 12 shows SDS PAGE analysis showing that core-shell particles protect chemokines from enzymatic degradation. Core-shell particles were incubated with the following chemokines, mucosae-associated epithelial chemokine (MEC/CCL28), stromal cell-derived factor-1 beta, (SDF-1β/CXCL12b), and eotaxin-2 (CCL24), in presence of trypsin. Solution of the chemokines (control) are shown in Lanes 1, 4, and 7. Chemokines incubated with particles (Lane 3, 6, and 9) are protected from tryptic degradation whereas chemokines not incubated with particles (Lane 2, 5, and 8) are susceptible to proteolytic digestion. The black boxes represent striped boxes represent light blots on the graphic.

SDS-PAGE analysis was used to evaluate the particles ability to protect chemokines, chosen as model, from enzymatic degradation. As shown in FIG. 12, trypsin rapidly degraded each class of chemokines in the absence of the sequestration by particles (FIG. 12, Lanes 2, 5, 8). In marked contrast, chemokines incubated with trypsin and particles (FIG. 12, Lane 3, 6, 9) generated a single species band that was not fragmented, suggesting that particles successfully preserved biomarkers from proteolysis.

Core-shell Particles Concentrate and Preserve PDGF Spiked in Human Serum

Figure 13:
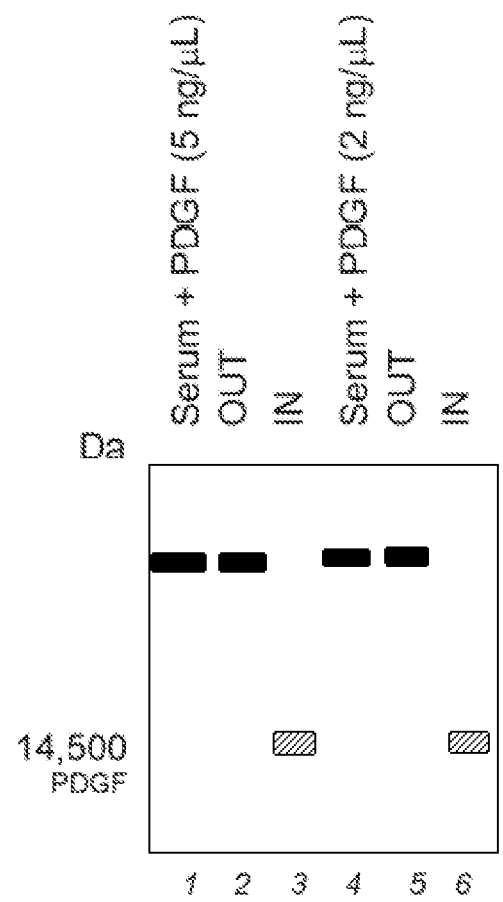
FIG. 13 shows immunoblot analysis demonstrating recovery of PDGF spiked in human serum. Lane 1) Human serum plus PDGF (5 ng/μL): when serum is not incubated with particles, PDGF cannot be detected; 2) particle supernatant (OUT); 3) particle content (IN); 4) Human serum plus PDGF (2 ng/μL): when serum is not incubated with particles, PDGF cannot be detected; 5) particle supernatant (OUT); 6) particle content (IN).

The extremely short half-life of PDGF in plasma (2 minutes) is a major analytical challenge. Immunoblotting and mass spectrometry were used to study the efficiency of core-shell particles to harvest, concentrate and preserve PDGF spiked in human serum. Immunoblotting was used to verify the preservation of PDGF by the presence of the correct molecular weight intact protein. Aliquots of 50 μL of core-shell particles were incubated with 50 μL of a solution with PDGF (at a concentration of 5 ng/mL or 2 ng/mL) spiked in human serum diluted 1:25 in 50 mM TrisHCl pH 7 for 1 hour at room temperature. The particles excluded the high molecular weight proteins which remained in the supernatant (FIG. 13, Lane 2 and 5) and at the same time concentrated PDGF (FIG. 13, Lane 3 and Lane 6) that was spiked in serum at two different concentrations. As shown above with the ELISA, PDGF in the starting solution was undetectable (FIG. 13, Lane 1 and 4). The particles increased the concentration of PDGF well above the immunoblot detection limit within an extraordinarily complex serum solution, with no detectable alteration in the mass or abundance of the PDGF molecule.

Materials and Methods

The serum used in this study was obtained under an IRB approved serum collection protocol (protocol number GMU HSRB #6081) under informed consent and the data were analyzed anonymously in compliance with HIPAA and the principles expressed in the Declaration of Helsinki.

Synthesis of core-shell hydrogel particles: Particles were synthesized using NIPAm (Sigma-Aldrich) and BIS (Sigma-Aldrich) by precipitation polymerization [49]. AAc (Sigma-Aldrich) was incorporated into NIPAm particle to provide a charge based affinity moiety bait for affinity capture of peptides and small molecules [9].

(NIPAm/AAc) core: NIPAm (0.184 g), BIS (0.0055 g), and AAc (48.4 μL) were dissolved in 30 mL of H2O and then passed through a 0.2 μm filter. The solution was purged with nitrogen for 15 min at room temperature and medium stir rate and then heated to 70° C. Ammonium persulfate (APS, Sigma-Aldrich, 0.0099 g) in 1 mL of H2O was added to the solution to initiate polymerization. After 10 minutes shell solution was added.

(NIPAm)shell: The shell solution was prepared by dissolving 0.736 g of NIPAm and 0.120 g of BIS in 10 ml of water. The solution was passed through a 0.2 μm filter and purged with nitrogen for 15 min at room temperature and medium stir rate. After 10 minutes from APS injection, shell solution was added to the reacting core solution. The reaction was maintained at 70° C. under nitrogen for 3 h and then cooled overnight. Particles were washed to eliminate un-reacted monomer by subsequent centrifugations at 16.1 rcf, 25° C., 15 minutes. Supernatant was disposed and particles re-suspended in 1 ml of water.

Characterization of Particles: The concentration of particles was assessed by weighing the lyophilized particles. Particles were counted by flow cytometry.

Particle size dependence on temperature and pH was determined via photon correlation spectroscopy (submicron particle size analyzer, Beckman Coulter). The pH of solution was controlled by adding proper amounts of NaOH, HCl with background electrolyte solution of KCl. Average values were calculated for three measurements using a 200 s integration time, and the solutions were allowed to thermally equilibrate for 10 min before each set of measurements. Measured values were then converted to particle sizes via the Stokes-Einstein relationship [54]. Particles were further characterized by atomic force microscopy (AFM) using an NSCRIPTORT™ DPN® System (NanoInk). Particle suspension in MilliQ water (pH 5.5, 1 μg/mL) was deposited on freshly cleaved mica under humid atmosphere at room temperature for 15 minutes and dried under nitrogen before measurement. Images were acquired under AC mode using a silicon tip with a typical resonance frequency of 300 kHz and a radius smaller than 10 nm.

Particle incubation: 50 μL of core-shell particles were incubated with 50 μL of solution containing:

0.02 mg/mL PDGF, 0.2 mg/mL BSA in 50 mM TrisHCl pH 7;

PDGF, BSA, aprotinin (MW 6,500 Da), lysozyme (MW 14,400 Da), trypsin inhibitor (MW 21,500 Da), carbonic anhydrase (MW 31,000 Da), and ovalbumin (MW 45,000

419 Da), each at a concentration of 0.05 mg/mL dissolved in 50 mM Tris pH 7.

mucosae-associated epithelial chemokine (MEC/CCL28, Antigenix America), stromal cell-derived factor-1 beta, (SDF-1β/CXCL12b, Antigenix America), and eotaxin-2-(CCL24, Antigenix America) each at a concentration of 0.02 mg/mL mixed with BSA (0.2 mg/mL) and dissolved in 50 mM Tris pH 7.

Incubations lasted 30 minutes at room temperature. After incubation, samples were centrifuged for 7 minutes, 25 C at 16.1 rcf and supernatant was saved. Then, the particles were re-suspended in 1 mL water and centrifuged for 7 minutes, 25 C at 16.1 rcf. Centrifugation and washing were repeated three times.

Particle elution of captured analytes: The particles were directly loaded on the gel when performing SDS-PAGE or immunoblot analysis. When performing ELISA and mass spectrometry analysis washed particles were incubated with elution buffer (60% acetonitrile-2% acetic acid) for 30 minutes and then centrifuged for 7 minutes, 25° C. at 16.1 rcf. Eluate was saved, a second elution step was performed and the eluate saved in the same vial. Samples were then dried with Speed Vac (ThermoFisher) and analyzed with ELISA or mass spectrometry.

SDS-PAGE analysis: Particles and supernatant deriving from particle incubation were loaded on 18% Tris Glycine gel (Invitrogen Corporation). The particles were retained in the stacking region of the gel while all of the captured proteins were electroeluted from particles and resolved in the gel. Proteins were detected by silver staining.

Enzymatic Degradation analysis: PDGF-BSA (Cell Signaling Technology) solution (0.11 mg/mL total protein) in 50 mM TrisHCl pH 7 was incubated with trypsin (Promega Corporation) at 1:100 w/w protein:protease ratio for different time periods (0, 10, 20, and 40 minutes) at 37° C. in order to study the degradation patterns over time. Core-shell particles were incubated for 1 hour at 37° C. in a 50 mM TrisHCl pH 7 solution containing PDGF-BSA (0.11 mg/mL total protein) and trypsin (0.0011 mg/mL).

Each of the following chemokines MEC/CCL28, SDF-1β/CXCL12b, CCL24 dissolved in 50 mM TrisHCl pH 7 at a concentration of 0.02 mg/mL was incubated separately with trypsin at 1:50 w/w protein:protease ratio and with core-shell particles for 40 minutes at 37° C.

Immunoblot analysis: Proteins were separated by 1-D gel electrophoresis in 18% Tris-Glycine gel as before, and then transferred onto Immobilion PVDF membrane (Millipore). The membrane was stained with SYPRO Ruby stain (MolecularProbes) according to vendor instructions. The protein blot was imaged using Kodak 4000 mM. The membrane was then incubated with PBS supplemented with 0.2% I-Block (Applied Biosystems/Tropix) and 0.1% Tween 20 (Sigma-Aldrich) for 1 hour at room temperature, and then with anti-body raised against PDGF-BB overnight at 4° C. under continuous agitation. After washes with PBS supplemented with 0.2% I-Block (w/v) and 0.1% Tween 20, immunoreactivity was revealed by using a specific horseradish peroxidase conjugated anti-IgG secondary antibody and the enhanced chemiluminescence system (Supersignal West Dura, ThermoFisher Scientific).

ELISA analysis: Particles were incubated with 1 mL of PDGF-BB standard (R&D System) diluted in Calibrator Diluent RD6-3. Incubation times, washings, and elutions were carried out as previously described. Eluate dried with Speed Vac was re-suspended in 100 μL of water with gentle vortexing and then an ELISA assay for Human PDGF-BB was performed according to manufacturer's instructions. Each measurement was carried out in duplicate and individual standard curves were generated for each set of samples assayed. Aliquots of 1 mL of PDGF solution below the detection limit of the kit (20 pg/mL) were incubated for 30 minutes with different numbers of particles (50, 100, 200, and 5000). Proteins were eluted from the washed particles by means of two subsequent elution steps with 60% acetonitrile and 2% acetic acid. ELISA readings were performed on a volume of 100 μL.

ELISA measurement of native serum PDGF was used to judge the particle capture yield for a series of particle concentrations introduced in serum. Aliquots of 1000 μL of serum diluted 1:10 in 50 mM Tris HCl pH were incubated with increasing quantities of particles (200, 500, 1000, and 1500 μL) for 30 minutes at room temperature. Particles were washed as previously described and incubated with 100 μL of elution buffer (60% acetonitrile-2% acetic acid) for 10 minutes and then centrifuged (7 minutes, 25° C. at 16.1 ref). Particle eluates were freeze dried and resuspended in Calibrator Diluent RD6-3, R&D Systems. Serum solution was diluted in Calibrator Diluent. ELISA readings were performed on a volume of 100 μL.

Mass spectrometry analysis: The following solutions were incubated with the core-shell particles:

PDGF spiked in complex protein mixture: a protein mixture containing 6.7 µg/mL BSA (ThermoFisher Scientific, MW 66,000), 6.7 µg/mL aprotinin (Sigma-Aldrich, MW 6,500 Da), 6.7 µg/mL lysozyme (Sigma-Aldrich, MW 14,400 Da), 6.7 µg/mL trypsin inhibitor (Invitrogen Corporation, MW 21,500 Da), 6.7 µg/mL carbonic anhydrase (Sigma-Aldrich, MW 31,000 Da), and 6.7 µg/mL ovalbumin (Sigma-Aldrich, MW 45,000 Da) in 50 mM TrisHCl pH 7 with a total protein concentration of 40 µg/482 mL was used. PDGF was added at the following concentrations: 670 ng/mL, 67 ng/mL, 6.7 ng/mL, 0.67 ng/mL so that the ratio between PDGF and the total protein was 1:60, 1:600, 1:6,000 and 1:60,000 respectively. Aliquots of 1.5 mL of solution were incubated with 100 µL of core-shell particles. Proteins were eluted with 60% acetonitrile and 2% acetic acid in a volume of 100 µL, eluates were dried with a Speed Vac (Thermo) and analyzed with nano reverse phase liquid chromatography mass spectrometry (RPLC-MS/MS). Aliquots of 100 µl were analyzed both from solution and eluates, thus maintaining the same volume.

human serum: 200 L of healthy donor serum was diluted 1:3 in TrisHCl buffer, pH 7 50 mM, with 100 L of core-shell particles. Particles were washed with 10% acetonitrile, 0.5×PBS buffer, and eluted with acetonitrile 60%, acetic acid 2%. Sample was dried with Speed Vac (Thermo) and analysed with nanoRPLC-MS/MS.

Eluates from the particles were analyzed with nanoRPLC-MS/MS. Proteins dried with Speed Vac were reconstituted in 8 M urea, reduced by 10 mM DTT, alkylated by 50 mM iodoacetamide, and digested by trypsin at 37° C. overnight. Tryptic peptides were further purified by Zip-Tip (Millipore) and analyzed by LC-MS/MS using a linear ion-trap mass spectrometer (LTQ, Orbitrap). After sample injection, the column was washed for 5 minutes with mobile phase A (0.4% acetic acid) and peptides eluted using a linear gradient of 0% mobile phase B (0.4% acetic acid, 80% acetonitrile) to 50% mobile phase B in 30 minutes at 250 nanoliter/min, then to 100% mobile phase B for an additional 5 minutes. The LTQ mass spectrometer was operated in a data-dependent mode in which each full MS scan was followed by five MS/MS scans where the five most abundant molecular ions were dynamically selected for collision induced dissociation (CID) using a normalized collision energy of 35%. Tandem mass spectra were searched against SEQUEST database using tryptic cleavage constraints. High-confidence peptide identifications were obtained by applying the following filters to the search results: cross-correlation score (XCorr)>=1.9 for 1+, 2.2 for 2+, 3.5 for 3+, and a maximum probability for a random identification of 0.01.

Mass spectrometry analysis of the solutions containing PDGF at a ratio of 1:60, 1:600 and 1:6,000 to total protein identified 13, 6, and 1 peptides belonging to human PDGF respectively, while eluates from core-shell particles contained 33, 15, 5 peptides respectively. At 1:60,000 PDGF to total protein ratio, PDGF peptides were not detected in the original solution after trypsin digestion for mass spectrometric analysis (PDGF concentration of 0.67 ng/mL), while eluates from the particles yielded a clear mass spectrometer detection spectra of the PDGF trypsin peptides. Thus core-shell particles increased the number of peptides, identified by mass spectrometry, from a solution when PDGF was present within the known detection level of the mass spectrometer. In addition, when this biomarker was diluted to less than one nanogram per mL and was masked by highly abundant proteins, the core-shell particles were able to concentrate PDGF and raise it into the detection range of mass spectrometry.

In order to further assess the capability of particles to concentrate and preserve PDGF in a physiologic medium, and to identify any proteins sequestered simultaneously, PDGF (at a concentration of 5 ng/µL) was spiked in human serum diluted 1:25 in 50 mM TrisHCl pH 7 and the solution was incubated with 50 µl of core-shell particles for 1 hour. Proteins were eluted, dried and analyzed with nanoRPLC-MS/MS. As shown in Table S1, PDGF was recovered and clearly identified with high peptide hit coverage by mass spectrometer analysis. A number of rare and low molecular weight proteins were identified, within the mixture of proteins captured by the core-shell particles. Additionally, core-shell particles were incubated with human serum and the proteins eluted from the particles were analyzed with nanoRPLC-MS/MS. Peptides belonging to native PDGF present in blood at very low abundance (~1 ng/mL) were identified.

These data support the use of the core-shell particles to harvest and preserve known biomarkers from serum, while providing a means to dramatically increase the concentration of biomarkers and the effective sensitivity of current biomarker measurement and discovery technology.

Overall, the present invention is an immunoassay system or device that includes a built in analyte enrichment and isolation step conducted by particles in a size range of 1 nm-100 µm containing an internal affinity bait, such that a) the sample fluid containing the analyte is exposed to a zone of nanoparticles that consist of an open polymeric meshwork enclosing an affinity bait that recognizes the analyte, b) analyte is concentrated, sequestered and protected from degradation INSIDE the particles, c) the analyte is released to be recognized by a labeled ligand or antibody. The immunoassay device is such that the particles are suspended in the analyte sample containing fluid, wherein the suspended particles are of such buoyancy that they remain in solution and do not settle by gravity, the particles are of an open polymeric structure such that they are greater than 80% occupied by the solute they are suspended in. The immunoassay device also is such that the mixture of particles and sample fluid is applied to the device such that the particles are deposited and immobilized into a zone within a fluid path within the lateral flow immunoassay device.

The present invention also is a point-of-care immunoassay device that includes analyte capture particles, such particles comprising: a polymeric matrix shell and an internal core containing an immobilized affinity ligand; wherein the polymeric matrix has a pore size that under certain conditions allows for the analyte to enter the polymeric matrix while excluding other compounds from the mixture from entering the polymeric matrix; wherein the affinity ligand recognizes the analyte of interest, and wherein the capture particles are incorporated into a porous substratum as part of a lateral flow immunoassay device. The flow path of the fluid sample can be altered after the particles have sequestered the analyte of interest. A method for separating analyte capture particles contains target analytes from cells present in a sample, wherein the capture particles flow within the immunoassay zones by wicking through different porosities, wherein the particles are in a size range from 1-1000 nanometers. The sample is whole blood or another body fluid, such as urine, cerebro-spinal fluid, sweat, saliva, nipple aspirates, or amniotic fluid; a non-biologic fluid; an environmental, agricultural, or food sample. The present invention also separates target biomarkers from capture particles, wherein an extraction buffer is utilized to remove the sequestered biomarkers from the capture particles. The sample is whole blood or another body fluid, such as urine, cerebro-spinal fluid, sweat, saliva, nipple aspirates, or amniotic fluid; a non-biologic fluid; an environmental, agricultural, or food sample.

The method for sequestering, concentrating and protecting proteins, peptides, or nucleic acid biomarkers from degradation, is such that wherein: contacting a mixture with a capture particle, comprising: a) a polymeric matrix; wherein the polymeric matrix has a pore size that under certain conditions allows for the analyte to enter the polymeric matrix while excluding other compounds from the mixture from entering the polymeric matrix; and b) an internal immobilized affinity bait, wherein a population of the capture particles containing multiple subpopulations specific for individual classes of low molecular weight molecules present in a sample are incorporated within a lateral flow immunoassay device. A means of pre-concentrating and preserving an analyte of the present invention also operate wherein a) the analyte is present in a fluid solution in the presence of hydrogel particles containing an affinity bait for the analyte, such that the particles are of sufficient small size and buoyancy to remain in solution and not to settle by gravity b) a high proportion of the analyte is sequestered within the particles, c) the bulk spent fluid volume is wicked away within a porous matrix. A capture-particle of the present invention comprises: a) a molecular sieve portion; and b) an analyte binding portion; wherein the molecular sieve portion, analyte binding portion or both further comprise a cross-linked region having modified porosity, and wherein the sieve portion contracts and/or expands in response to physical and/or chemical treatment so as to trap analyte within the capture particle. The analyte binding portion comprises at least one type of moiety capable of chemically or electrostatically binding or sequestering an analyte. The analyte binding portion comprises a carboxy group, amine group, lipid, phosphoprotein, phospholipids, amide group, hydroxyl group, ester group, acrylic group, thiol group, acrylic acid, antibodies, binding proteins, binding pairs, metals, chelating agents, nucleic acids, aptamers, enzyme-binding pockets, lectins, pharmacologic agent, synthetic peptides, antibody fragments, hydrophobic surface, hydrophilic surface, any derivatives thereof or a combination thereof. An analyte is bound to the analyte binding portion, the analyte comprising: organic molecules, inorganic molecules, polypeptides, carbohydrates, nucleic acids, lipids, derivatives thereof or any combination thereof. The molecular sieve portion is an outer shell enclosing an inner core, the inner core comprising the analyte binding portion. The molecular sieve portion, analyte binding portion or both comprise: polyacrylamide, poly(N-isopropylacrylamide), N-alkyl substituted polyacrylamide, poly(N-vinylalkylamide), poly(methacrylic acid), poly(benzyl glutamate), poly (2-ethylacrylic acid), poly(4-vinylpyridine), derivatives thereof or any combination thereof. The cross-linked region comprises N,N-methylenebisacrylamide, ethylene glycol dimethacrylate, tetraethylene glycol dimethacrylate, poly (ethyleneglycol)dimethacrylate or any combination thereof. The molecular sieve portion, analyte binder portion or both comprise a hydrogel. The capture-particle releases a bonded or sequestered analyte when exposed to a physical or chemical treatment, wherein the physical or chemical treatment comprises exposure to: electrical charge, hydrostatic pressure, change in pH, change in temperature, acidic agent, basic agent, UV, ultrasound, x-ray, or a combination thereof.

References
1. Liotta L A, Ferrari M, Petricoin E (2003) Clinical proteomics: written in blood. Nature 425: 905.
2. Anderson N L, Anderson N G (2002) The human plasma proteome: history, character, and diagnostic prospects. Mol Cell Proteomics 1: 845-867.
3. Petricoin E F, Ardekani A M, Hitt B A, Levine P J, Fusaro V A, et al. (2002) Use of proteomic patterns in serum to identify ovarian cancer. Lancet 359: 572-577.
4. Merrell K, Southwick K, Graves S W, Esplin M S, Lewis N E, et al. (2004) Analysis of low abundance, low-molecular-weight serum proteins using mass spectrometry. J Biomol Tech 15: 238-248.
5. Petricoin E F, Belluco C, Araujo R P, Liotta L A (2006) The blood peptidome: a higher dimension of information content for cancer biomarker discovery. Nat Rev Cancer 6: 961-967.
6. Lopez M F, Mikulskis A, Kuzdzal S, Bennett D A, Kelly J, et al. (2005) High-resolution serum proteomic profiling of Alzheimer disease samples reveals disease-specific, carrier-protein bound mass signatures. Clin Chem 51: 1946-1954.
7. Zhou M, Lucas D A, Chan K C, Issaq H J, Petricoin E F, 3rd, et al. (2004) An investigation into the human serum "interactome". Electrophoresis 25: 1289-1298.
8. Ayache S, Panelli M, Marincola F M, Stroncek D F (2006) Effects of storage time and exogenous protease inhibitors on plasma protein levels. Am J Clin Pathol 126: 174-184.
9. Luchini A, Geho D H, Bishop B, Tran D, Xia C, et al. (2008) Smart hydrogel particles: biomarker harvesting: one-step affinity purification, size exclusion, and protection against degradation. Nano Lett 8: 350-361.
10. Hoffman A S (2002) Hydrogels for biomedical applications. Adv Drug Deliv Rev 54: 3-12.
11. Drury J L, Mooney D J (2003) Hydrogels for tissue engineering: scaffold design variables and applications. Biomaterials 24: 4337-4351.
12. Bowen-Pope D F, Malpass T W, Foster D M, Ross R (1984) Platelet-derived 541 growth factor in vivo: levels, activity, and rate of clearance. Blood 64: 458-469.
13. Hennink W E, van Nostrum C F (2002) Novel crosslinking methods to design hydrogels. Adv Drug Deliv Rev 54: 13-36.
14. Pelton R (2000) Temperature-sensitive aqueous microgels. Adv Colloid Interface Sci 85: 1-33
15. Nayak S, Gan D, Serpe M J, Lyon L A (2005) Hollow thermoresponsive microgels. Small 1: 416-421.
16. Fortina P, Kricka L J, Surrey S, Grodzinski P (2005) Nanobiotechnology: the promise and reality of new approaches to molecular recognition. Trends Biotechnol 23: 168-173.
17. Moghimi S M, Hunter A C, Murray J C (2005) Nanomedicine: current status and future prospects. FASEB J 19: 311-330.
18. Sakamoto J H, Smith B R, Xie B, Rokhlin S I, Lee S C, et al. (2005) The molecular analysis of breast cancer utilizing targeted nanoparticle based ultrasound contrast agents. Technol Cancer Res Treat 4: 627-636.
19. Li X, Ponten A, Aase K, Karlsson L, Abramsson A, et al. (2000) PDGF-C is a new protease activated ligand for the PDGF alpha-receptor. Nat Cell Biol 2: 302-309.
20. Fredriksson L, Li H, Eriksson U (2004) The PDGF family: four gene products from five dimeric isoforms. Cytokine Growth Factor Rev 15: 197-204.
21. Heinrich M C, Corless C L, Duensing A, McGreevey L, Chen C J, et al. (2003) PDGFRA activating mutations in gastrointestinal stromal tumors. Science 299: 708-710.
22. Baxter E J, Hochhaus A, Bolufer P, Reiter A, Fernandez J M, et al. (2002) The t(4;22)(q12;q11) in atypical chronic myeloid leukaemia fuses BCR to PDGFRA. Hum Mol Genet. 11: 1391-1397.

23. Yu J, Ustach C, Kim H R (2003) Platelet-derived growth factor signaling and human cancer. J Biochem Mol Biol 36: 49-59.
24. Board R, Jayson G C (2005) Platelet-derived growth factor receptor (PDGFR): a target for anticancer therapeutics. Drug Resist Updat 8: 75-83.
25. Kabbinavar F, Hurwitz H I, Fehrenbacher L, Meropol N J, Novotny W F, et al. (2003) Phase II, randomized trial comparing bevacizumab plus fluorouracil (FU)/leucovorin (LV) with FU/LV alone in patients with metastatic colorectal cancer. J Clin Oncol 21: 60-65.
26. McArthur G A, Demetri G D, van Oosterom A, Heinrich M C, Debiec-Rychter M, et al. (2005) Molecular and clinical analysis of locally advanced dermatofibrosarcoma protuberans treated with imatinib: Imatinib Target Exploration Consortium Study B2225. J Clin Oncol 23: 866-873.
27. Mathew P, Thall P F, Jones D, Perez C, Bucana C, et al. (2004) Platelet-derived growth factor receptor inhibitor imatinib mesylate and docetaxel: a modular phase I trial in androgen independent prostate cancer. J Clin Oncol 22: 3323-3329.
28. Kubo T, Piperdi S, Rosenblum J, Antonescu C R, Chen W, et al. (2008) Platelet-derived growth factor receptor as a prognostic marker and a therapeutic target for imatinib mesylate therapy in osteosarcoma. Cancer 112: 2119-2129.
29. Kagami S, Kakinuma T, Saeki H, Tsunemi Y, Fujita H, et al. (2005) Increased serum CCL28 levels in patients with atopic dermatitis, psoriasis vulgaris and bullous pemphigoid. J Invest Dermatol 124: 1088-1090.
30. Jahnz-Rozyk K, Targowski T, Glodzinska-Wyszogrodzka E, Plusa T (585 2003) Cc-chemokine eotaxin as a marker of efficacy of specific immunotherapy in patients with intermittent IgE587 mediated allergic rhinoconjunctivitis. Allergy 58: 595-601.
31. Robak E, Kulczycka L, Sysa-Jedrzejowska A, Wierzbowska A, Robak T (2007) Circulating proangiogenic molecules PIGF, SDF-1 and sVCAM-1 in patients with systemic lupus erythematosus. Eur Cytokine Netw 18: 181-187.
32. Baggiolini M, Dewald B, Moser B (1994) Interleukin-8 and related chemotactic cytokines—CXC and CC chemokines. Adv Immunol 55: 97-179.
33. Frederick M J, Clayman G L (2001) Chemokines in cancer. Expert Rev Mol Med 3: 1-18.
34. Braude E A, Nachod F C (1955) Determination of Organic Structures by Physical Methods. New York: Academic Press.
35. Denizli A, Piskin E (2001) Dye-ligand affinity systems. J Biochem Biophys Methods 49: 391-416.
36. Sereikaite J, Bumelis V A (2006) Examination of dye-protein interaction by gel-permeation chromatography. Biomed Chromatogr 20: 195-199.
37. Fredolini C, Meani F, Reeder K A, Rucker S, Patanarut A, et al. (2008) Concentration and Preservation of Very Low Abundance Biomarkers in Urine, such as Human Growth Hormone (hGH), by Cibacron Blue F3G-A Loaded Hydrogel Particles. Nano Res 1: 502-518.
38. Uekama K, Hirayama F, Arima H (2006) Recent Aspect of Cyclodextrin-Based Drug Delivery System. J Inclusion Phenom Macrocyclic Chem 56: 3-8.
39. Jin S, Lee Y, Kang H Methyl-β-cyclodextrin, a specific cholesterol-binding agent, inhibits melanogenesis in human melanocytes through activation of ERK. Arch Dermatol Res 8: 451-454.
40. Cai W, Yao X, Shao X, Pan Z (2005) Bimodal Complexations of Steroids with Cyclodextrins by a Flexible Docking Algorithm. J Inclusion Phenom Macrocyclic Chem 51: 41-51.
41. Borst C, Holzgrabe U (2008) Enantioseparation of dopa and related compounds by cyclodextrin-modified microemulsion electrokinetic chromatography. J Chromatogr A.42. Dodziuk H (2006) Cyclodextrins and Their Complexes: Chemistry, Analytical Methods, Applications. Hoboken: Wiley-VCH.
43. Elmas B, Onur M, Senel S, Tuncel A (2002) Temperature controlled RNA isolation by N616 isopropylacrylamide-vinylphenyl boronic acid copolymer latex. Colloid Polym Sci 280: 1137-1146.
44. Kataoka K, Miyazaki H, Okano T, Sakurai Y (1994) Sensitive Glucose-Induced Change of the Lower Critical Solution Temperature of Poly[N,N-(dimethylacrylamide)-co-3-(acrylamido)-phenylboronic acid] in Physiological Saline. Macromolecules 27: 1061-1062.
45. Lorand J P, Edwards J O (1959) Polyol Complexes and Structure of the Benzeneboronate Ion. J Org Chem 24: 769-774.
46. Mader H S, Wolfbeis O S (2008) Boronic acid based probes for microdetermination of saccharides and glycosylated biomolecules. Mikrochim Acta 162: 1-34.
47. Yamauchi A, Suzuki I, Hayashita T (2006) Saccharide recognition by Boronic Acid Fluorophore/Cyclodextrin Complexes in Water. In: Geddes CDL, Joseph R. editor. Glucose Sensing, Topics in Fluorescence Spectroscopy: Springer. pp. 237-258.
48. Zhang Y, Gao X, Hardcastle K, Wang B (2006) Water-soluble fluorescent boronic acid compounds for saccharide sensing: substituent effects on their fluorescence properties. Chemistry 12: 1377-1384.
49. Jones C D, Lyon L A (2000) Synthesis and Characterization of Multiresponsive 631 Core-Shell Microgels. Macromolecules 33: 8301-8306.
50. Couvreur P, Reddy L H, Mangenot S, Poupaert J H, Desmaele D, et al. (2008) Discovery of new hexagonal supramolecular nanostructures formed by squalenoylation of an anticancer nucleoside analogue. Small 4: 247-253.
51. Cho E C, Kim J W, Fernandez-Nieves A, Weitz D A (2008) Highly responsive hydrogel scaffolds formed by three-dimensional organization of microgel nanoparticles. Nano Lett 8: 168-172.
52. Smith E R, Zurakowski D, Saad A, Scott R M, Moses M A (2008) Urinary biomarkers predict brain tumor presence and response to therapy. Clinical cancer research 14: 2378-2386.
53. Barratt J, Topham P (2007) Urine proteomics: the present and future of measuring urinary protein components in disease. CMAJ 177: 361-368.
54. Pecora R (1985) Dynamic Light Scattering: Applications of Photo Correlation Spectroscopy: Springer. 436 p.

We claim:

1. A method of analyte enrichment in an immunoassay, the method comprising:
providing an immunoassay device comprising a wicking matrix upstream of a porous matrix and an analyte binding region downstream of said porous matrix;
adding a sample fluid containing the analyte to porous hydrogel nanoparticles and allowing the analyte to sequester within the porous hydrogel nanoparticles, wherein said porous hydrogel nanoparticles i) range in size from 1 nm to 100 μm; ii) contain an analyte specific affinity bait internally within the particles for immobilization of the analyte; and iii) comprise an open polymeric meshwork that encloses the affinity bait;

allowing the sample fluid of to pass through the wicking matrix into the porous matrix; and trapping the porous hydrogel nanoparticles into the porous matrix;

wherein the pore size of the porous matrix is such that the porous hydrogel nanoparticles do not migrate within the porous matrix and thereby the porous hydrogel nanoparticles are trapped at the entry point of the fluid to the porous matrix once the complete volume of sample fluid has passed from the wicking matrix to the porous matrix, enclosing therein the sequestered analyte for subsequent elution into the analyte binding region for immunoassay analysis of the analyte.

* * * * *